(12) United States Patent
Ishii et al.

(10) Patent No.: US 12,009,626 B2
(45) Date of Patent: Jun. 11, 2024

(54) LASER DEVICE, MULTI-WAVELENGTH LASER DEVICE, AND PHOTOACOUSTIC MEASUREMENT APPARATUS

(71) Applicant: FUJIFILM Corporation, Tokyo (JP)

(72) Inventors: Hiroyasu Ishii, Kanagawa (JP); Takatsugu Wada, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 944 days.

(21) Appl. No.: 17/017,804

(22) Filed: Sep. 11, 2020

(65) Prior Publication Data

US 2020/0412078 A1 Dec. 31, 2020

Related U.S. Application Data

(63) Continuation of application No. PCT/JP2019/001211, filed on Jan. 17, 2019.

(30) Foreign Application Priority Data

Mar. 29, 2018 (JP) .................................. 2018-066075

(51) Int. Cl.
*H01S 3/08* (2023.01)
*A61B 5/00* (2006.01)
(Continued)

(52) U.S. Cl.
CPC ..... *H01S 3/08054* (2013.01); *G01N 29/2418* (2013.01); *G02B 5/3066* (2013.01);
(Continued)

(58) Field of Classification Search
USPC .......................................................... 372/12
See application file for complete search history.

(56) References Cited

U.S. PATENT DOCUMENTS

| 6,078,606 A * | 6/2000 | Naiman .................. F41G 3/145 |
| | | 372/17 |
| 2014/0185634 A1 | 7/2014 | Ichihara et al. |
| 2016/0226214 A1* | 8/2016 | Ishii ....................... H01S 3/092 |

FOREIGN PATENT DOCUMENTS

| JP | 2013-089680 A | 5/2013 |
| JP | 2013-214703 A | 10/2013 |

(Continued)

OTHER PUBLICATIONS

International Search Report issued in PCT/JP2019/001211; dated Apr. 10, 2019.

(Continued)

*Primary Examiner* — Tuan N Nguyen
(74) *Attorney, Agent, or Firm* — Studebaker & Brackett PC

(57) ABSTRACT

The laser device includes a laser crystal, a resonator including a pair of mirrors between which the laser crystal is interposed, a Q switch that is disposed on an optical path of the resonator and controls a Q value of the resonator, and a Brewster thin-film polarizer that is disposed on the optical path of the resonator and transmits selectively p-polarized light. The thin-film polarizer has wavelength selectivity in which a p-polarized light transmittance at a first wavelength exhibiting a maximum gain of the laser crystal is 5% or more to 25% or less, the p-polarized light transmittance monotonically increases as a wavelength becomes longer than the first wavelength, and a maximum transmittance is exhibited at a third wavelength. The laser device oscillates laser light at a second wavelength that is a wavelength longer than the first wavelength and shorter than or equal to the third wavelength.

18 Claims, 6 Drawing Sheets

(51) Int. Cl.
  *G01N 29/24* (2006.01)
  *G02B 5/30* (2006.01)
  *H01S 3/115* (2006.01)
  *H01S 3/16* (2006.01)
  *H01S 3/23* (2006.01)
(52) U.S. Cl.
  CPC ............ *H01S 3/115* (2013.01); *H01S 3/1633* (2013.01); *H01S 3/23* (2013.01); *A61B 5/0095* (2013.01)

(56) References Cited

FOREIGN PATENT DOCUMENTS

| JP | 2015-111660 A | 6/2015 |
| JP | 2015-191918 A | 11/2015 |

OTHER PUBLICATIONS

International Preliminary Report on Patentability and Written Opinion issued in PCT/JP2019/001211; dated Sep. 29, 2020.

\* cited by examiner

LASER DEVICE, MULTI-WAVELENGTH LASER DEVICE, AND PHOTOACOUSTIC MEASUREMENT APPARATUS

CROSS-REFERENCE TO RELATED APPLICATIONS

This application is a Continuation of PCT International Application No. PCT/JP2019/001211 filed on Jan. 17, 2019, which claims priority under 35 U.S.C § 119(a) to Japanese Patent Application No. 2018-066075 filed on Mar. 29, 2018. Each of the above applications is hereby expressly incorporated by reference, in its entirety, into the present application.

BACKGROUND OF THE INVENTION

1. Field of the Invention

The present invention relates to a laser device, a multi-wavelength laser device, and a photoacoustic measurement apparatus.

2. Description of the Related Art

Photoacoustic imaging by which the inside of a living body is imaged by utilizing a photoacoustic effect is known as a kind of imaging examination method capable of non-invasively examining the state of the inside of the living body. In the photoacoustic imaging, the inside of a living body is usually irradiated with pulsed light such as pulsed laser light. Inside the living body irradiated with the pulsed light, the volume of a living tissue that has absorbed energy of the pulsed light expands due to heat, and ultrasonic waves (photoacoustic signals) are generated. Visualization of the inside of the living body based on the photoacoustic signals is enabled by detecting the photoacoustic signals by using an ultrasonic probe or the like and by constructing a photoacoustic image based on the detected signals.

Regarding a laser device that can be used for photoacoustic wave measurement, for example, the use of alexandrite crystal, Ti:sapphire crystal, or the like for a laser medium is known. To enable stable oscillation in a laser device including alexandrite crystal as a laser medium, JP2015-111660A proposes a configuration including a non-coated Brewster polarizer or a configuration including a Brewster polarizer having a separation film that separates light in which the polarization direction is a predetermined direction and light in which the polarization direction is orthogonal to the predetermined direction from each other.

Many living tissues have an optical absorption property varying in accordance with light wavelength and typically each have a unique optical absorption property. As an example, FIG. 9 illustrates molecular absorption coefficients by light wavelength of oxidized hemoglobin (hemoglobin that is bound with oxygen: oxy-Hb) included abundantly in human arteries and reduced hemoglobin (hemoglobin that is not bound with oxygen: deoxy-Hb) included abundantly in veins. The optical absorption property of oxygenated hemoglobin corresponds to the optical absorption property of arteries, and the optical absorption property of deoxygenated hemoglobin corresponds to the optical absorption property of veins. A photoacoustic image generation method in which, by utilizing the difference of such optical absorbance in accordance with wavelength, a vascular portion is irradiated with kinds of light at two different wavelengths and arteries and veins are imaged while being distinguished from each other is known.

For example, JP2013-089680A, JP2013-214703A, and JP2015-191918A describe dual-wavelength laser devices capable of emitting such above-described kinds of light at two different wavelengths. Such laser devices each include alexandrite as a laser crystal and are capable of laser oscillation at a wavelength of 755 nm and a wavelength of 800 nm.

SUMMARY OF THE INVENTION

As described above, in a laser device, it may be desired to perform laser oscillation at a wavelength different from the maximum gain wavelength of the included laser crystal. JP2015-111660A does not mention wavelength selectivity at all.

In contrast, in JP2013-089680A, the laser device including alexandrite crystal includes a branching unit that branches an optical path by wavelength dispersion, a reflecting member having wavelength selectivity to reflect light at a wavelength of 755 nm, and a reflecting member having wavelength selectivity to reflect light at a wavelength of 800 nm. Due to the configuration, the laser device of JP2013-089680A is capable of laser oscillation at the maximum gain wavelength (755 nm) of a laser medium and at a wavelength of 800 nm that differs from the maximum gain wavelength.

In addition, the alexandrite crystal-included laser device of JP2013-214703A includes a wavelength switching unit that inserts a long-path filter into an optical path. The long-path filter transmits light at a wavelength of 800 nm at a high light transmittance of, for example, 99.8% while hardly transmitting light at a wavelength of 755 nm. The laser device of JP2013-214703A is capable of oscillating light at a wavelength of 800 nm when the long-path filter is inserted and capable of oscillating light at a wavelength of 755 nm when the long-path filter is not inserted.

The laser device of JP2015-191918A includes a Q-value changing unit, a resonator for a wavelength of 755 nm, and a resonator for a wavelength of 800 nm, and laser light oscillation at a wavelength of 755 nm and laser light oscillation at a wavelength of 800 nm are switched by changing the Q value.

For imaging all blood vessels at equivalent luminance, as opposed to imaging veins and arteries distinguishably by performing measurement by using two different wavelengths, it is preferable to perform measurement using light at a wavelength near 800 nm that is the crossover point of the absorption coefficients of the vein and the artery in FIG. 9.

However, in alexandrite crystal, the light emission efficiencies (gains) of light at a wavelength of 755 nm and light at a wavelength of 800 nm differ considerably from each other. FIG. 10 is a graph schematically illustrating the relation between the oscillation wavelength of the alexandrite crystal and the gain thereof. As will be understood by the graph, the gain of the alexandrite crystal is maximized near a wavelength of 755 nm and decreases as the wavelength becomes longer than 755 nm.

With respect to a wavelength of 755 nm that is the maximum gain wavelength of the laser medium, the gain of light at a wavelength of 800 nm is considerably low, and large electric power has to be supplied to perform oscillation. Thus, an increase in the size of devices and an increase in costs are caused. Moreover, laser power decreases when light at a wavelength of 800 nm is oscillated because the gain is not sufficient, and, when a photoacoustic image is picked up, there is a problem that the signal-to-noise ratio (S/N ratio) of an obtainable signal decreases.

The present invention has been made considering the above-described circumstances, and an object thereof is to provide a laser device, a multi-wavelength laser device, and a photoacoustic measurement apparatus that are capable of suppressing an increase in the size of devices, an increase in costs, and a decrease in output, even when laser oscillation is performed at a wavelength having a gain lower than the maximum gain of a laser medium.

A laser device of the present invention includes a laser crystal,
- a resonator including a pair of mirrors between which the laser crystal is interposed,
- a Q switch that is disposed on an optical path of the resonator and controls a Q value of the resonator, and
- a Brewster thin-film polarizer that is disposed on the optical path of the resonator and transmits selectively p-polarized light,
- the thin-film polarizer has wavelength selectivity in which a p-polarized light transmittance at a first wavelength exhibiting a maximum gain of the laser crystal is 5% or more to 25% or less, the p-polarized light transmittance monotonically increases as a wavelength becomes longer than the first wavelength, and a maximum transmittance is exhibited at a third wavelength, and
- the laser device oscillates laser light at a second wavelength that is a wavelength longer than the first wavelength and shorter than or equal to the third wavelength and that exhibits a p-polarized light transmittance of 90% or more in the thin-film polarizer.

In the laser device of the present invention, the p-polarized light transmittance of the thin-film polarizer may be 20% or less at the first wavelength and 95% or more at the second wavelength.

In the laser device of the present invention, a deference in wavelength between the first wavelength and the second wavelength is preferably less than 45 nm.

In the laser device of the present invention, the difference in wavelength between the first wavelength and the second wavelength is preferably 40 nm or less.

In the laser device of the present invention, when a gain at the first wavelength of the laser crystal is 1, a gain at the second wavelength of the laser crystal is Z, the p-polarized light transmittance at the first wavelength of the thin-film polarizer is X, and the p-polarized light transmittance at the second wavelength of the thin-film polarizer is Y, $$1 \times X^2 < Z \times Y^2$$

is preferably satisfied.

In the laser device of the present invention, when the maximum gain of the laser crystal is 1, the gain at the second wavelength of the laser crystal is preferably 0.7 or more.

In the laser device of the present invention, the first wavelength is preferably 755 nm±5 nm, and the second wavelength is preferably 780 nm±10 nm. In this case, the laser crystal can be alexandrite crystal.

In the laser device of the present invention, the first wavelength is preferably 800 nm±5 nm, and the second wavelength is preferably 835 nm±10 nm. In this case, the laser crystal can be Ti:sapphire crystal.

A multi-wavelength laser device of the present invention includes a first laser unit that oscillates first laser light at a first wavelength,

- a second laser unit that oscillates second laser light at a second wavelength that is a wavelength longer than the first wavelength, and
- a wave-combining unit that causes an optical path of the first laser light output from the first laser unit and an optical path of the second laser light output from the second laser unit to coincide with each other,
- the second laser unit is the laser device of the present invention, and
- the first laser unit is a laser device that has the same configuration as the second laser unit and that includes a non-coated Brewster polarizer instead of the Brewster thin-film polarizer.

A first photoacoustic measurement apparatus of the present invention includes the laser device of the present invention and
- a photoacoustic wave detection unit that detects a photoacoustic wave generated in a subject when the subject is irradiated with laser light at the second wavelength emitted from the laser device.

A second photoacoustic measurement apparatus of the present invention includes the multi-wavelength laser device and
- a photoacoustic wave detection unit that detects a photoacoustic wave generated in a subject when the subject is irradiated with the first laser light emitted from the multi-wavelength laser device and detects a photoacoustic wave generated in the subject when the subject is irradiated with the second laser light emitted from the multi-wavelength laser device.

The laser device of the present invention has the Brewster thin-film polarizer in the resonator. The thin-film polarizer has the wavelength selectivity in which the p-polarized light transmittance of the first wavelength exhibiting the maximum gain of the laser crystal is 5% or more to 25% or less, the p-polarized light transmittance monotonically increases toward a side of a wavelength longer than the first wavelength, and the maximum value is exhibited at the third wavelength. The laser device oscillates laser light at the second wavelength that is a wavelength longer than the first wavelength and shorter than or equal to the third wavelength and that exhibits a p-polarized light transmittance of 90% or more in the thin-film polarizer. Due to such a configuration, according to the laser device of the present invention, it is possible to suppress an increase in the size of the device, an increase in costs, and a decrease in output, even when laser oscillation is performed at a wavelength having a gain lower than the maximum gain of the laser medium.

DESCRIPTION OF THE PREFERRED EMBODIMENTS

Figure 1:
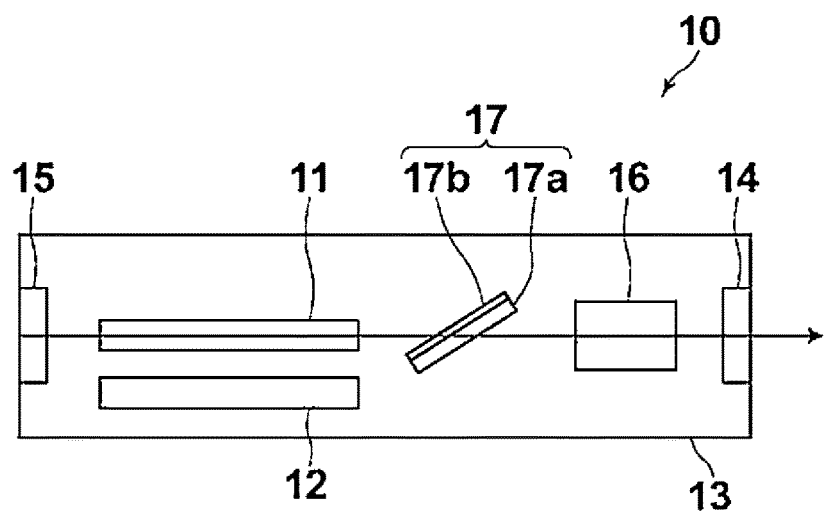
FIG. 1 is a schematic view of a configuration of a laser device of an embodiment of the present invention.

Hereinafter, embodiments of the present invention will be described in detail with reference to the drawings. To facilitate visibility, the size or the like of each component in the drawings differs as appropriate from the actual size thereof.

Laser Device

FIG. 1 is a schematic view of a configuration of a laser device according to an embodiment of the present invention. A laser device 10 has a laser rod 11, a flash lamp 12, a laser chamber 13, a pair of mirrors 14 and 15, a Q switch 16, a Brewster thin-film polarizer 17. The laser rod 11 is a laser medium in which a laser crystal is formed to have a rod shape. The laser device 10 oscillates laser light at a second wavelength that is longer than a first wavelength exhibiting the maximum gain of a laser crystal. The gain at the second wavelength is smaller than that at the first wavelength.

For example, alexandrite crystal or Ti:sapphire crystal can be used for the laser rod 11. Here, a case in which the alexandrite crystal is used will be described. The gain in laser oscillation of the alexandrite crystal peaks at a wavelength around 755 nm (refer to FIG. 4). The gain monotonically decreases as a wavelength becomes shorter in a wavelength below 755 nm and monotonically increases as the wavelength becomes longer in a wavelength above 755 nm.

The flash lamp 12 is an excitation light source and emits excitation light for exciting the laser rod 11. The laser rod 11 and the flash lamp 12 are accommodated in the laser chamber 13. The laser chamber 13 has space for accommodating the laser rod 11 and the flash lamp 12 therein. A reflection surface is formed inside the laser chamber 13, and the laser rod 11 is irradiated directly with light emitted from the flash lamp 12 or irradiated with light emitted from the flash lamp 12 and reflected by the reflection surface. The inside of the laser chamber 13 may be a diffuse reflection surface. A light source other than the flash lamp 12 may be used as an excitation light source.

The mirrors 14 and 15 face each other with the laser rod 11 therebetween and constitute a resonator. The optical path in the optical resonator is not necessarily linear, and the optical axis may be bent by providing a prism on the optical path between the mirrors 14 and 15. The mirror 14 is an output coupler (OC), and the mirror 15 is a total reflection mirror. The reflectance of the mirror 14 is preferably 70% or more. Laser light that is output light is emitted from the mirror 14.

The Q switch 16 is disposed on the optical path of the resonator and controls the Q value of the resonator. In FIG. 1, the Q switch 16 is disposed on the optical axis of the light induced and emitted by the laser rod 11 between the laser rod 11 and the mirror 14. The Q switch 16 may be disposed between the laser rod 11 and the mirror 15. The Q switch 16 changes the polarized state of transmitted light in accordance with an applied voltage. For example, a Pockels cell is used for the Q switch 16. Pulsed laser light can be obtained by rapidly changing insertion loss in the optical resonator from a large loss (low Q) to a small loss (high Q) by using the Q switch 16.

The Brewster thin-film polarizer 17 is disposed on the optical path of the resonator. In the laser device 10 of the present embodiment, the thin-film polarizer 17 is disposed between the laser rod 11 and the Q switch 16 in the resonator. The thin-film polarizer 17 may be disposed between the laser rod 11 and the mirror 15.

The Brewster thin-film polarizer 17 has a glass plate 17a of silica glass, borosilicate glass, or the like and a thin film 17b. The thin film 17b of the Brewster thin-film polarizer 17 is disposed such that the incidence angle of the laser light on the thin film 17b is a Brewster's angle. The thin film 17b is, for example, a dielectric multilayer reflecting film that exhibits high transmittance for p-polarized light and reflects s-polarized light.

Figure 2:
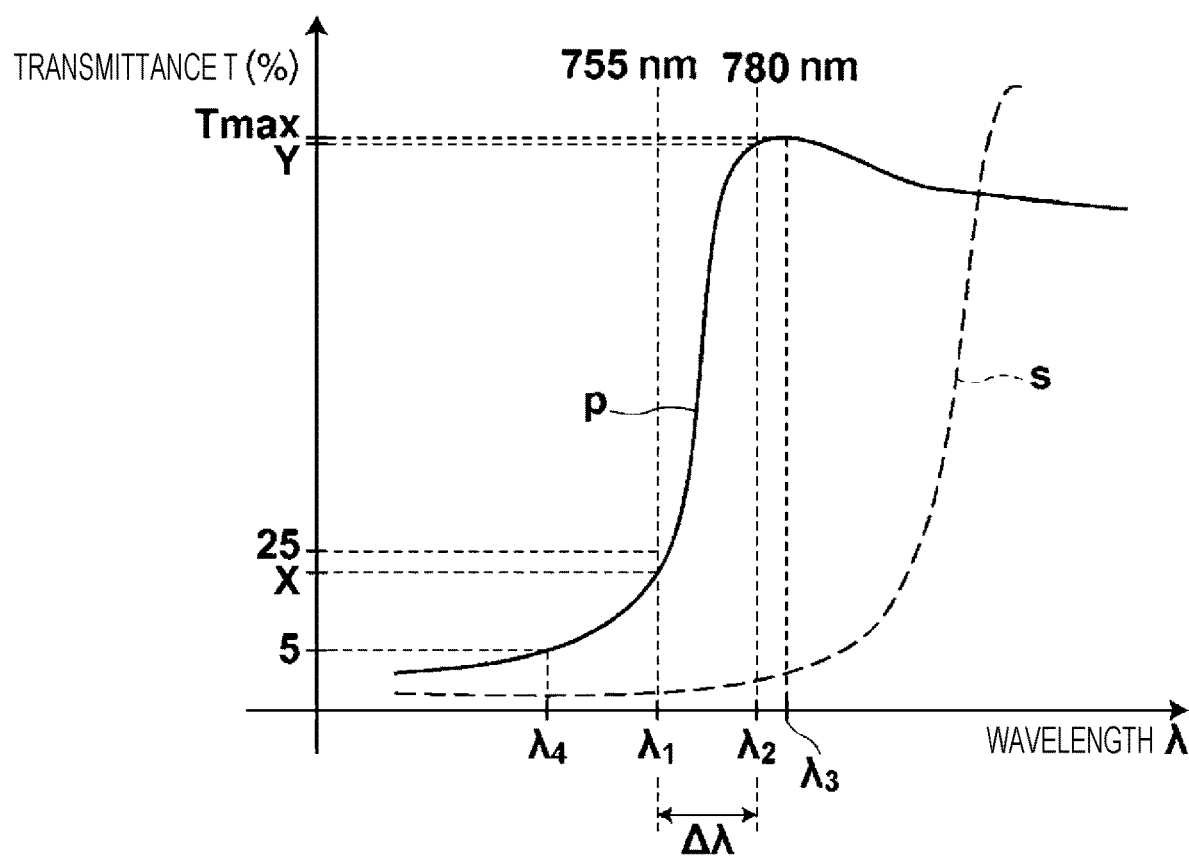
FIG. 2 illustrates wavelength characteristics of transmittance of a Brewster thin-film polarizer.

FIG. 2 illustrates an example of the wavelength characteristic of transmittance regarding the thin-film polarizer 17. In FIG. 2, the solid line indicates the p-polarized light transmittance, and the dashed line indicates the s-polarized light transmittance. The thin-film polarizer 17 has wavelength selectivity in which a p-polarized light transmittance X of a first wavelength $\lambda_1$ exhibiting the maximum gain of the laser crystal is 5% or more to 25% or less, the p-polarized light transmittance monotonically increases toward a side of a wavelength longer than the first wavelength $\lambda_1$, and the maximum transmittance $T_{max}$ is exhibited at a third wavelength $\lambda_3$. The first wavelength $\lambda_1$ is preferably a wavelength in which the p-polarized light transmittance X is 20% or less. Regarding the wavelength characteristic of transmittance, when a wavelength in which the p-polarized light transmittance is 5% is to be a fourth wavelength $\lambda_4$, the relation is denoted as $\lambda_4 \leq \lambda_1$.

The second wavelength $\lambda_2$ that is an oscillation wavelength of the laser device 10 is longer than the first wavelength $\lambda_1$ and shorter than or equal to the third wavelength $\lambda_3$, and exhibits a p-polarized light transmittance Y of 90% or more in the thin-film polarizer. That is, the second wavelength $\lambda_2$ is denoted by $\lambda_1 < \lambda_2 \leq \lambda_3$, and the transmittance Y thereof is denoted by $90\% < Y \leq T_{Max}$. $T_{max}$ is normally 97% or more to less than 100%. The second wavelength $\lambda_2$ is preferably a wavelength exhibiting a p-polarized light transmittance Y of 95% or more. The second wavelength $\lambda_2$ is most preferably a wavelength in which the transmittance Y exhibits the maximum value $T_{max}$.

That is, as illustrated in FIG. 2, it is preferable that the first wavelength $\lambda_1$ and the second wavelength $\lambda_2$ be positioned in the region in which, in the wavelength characteristic of the p-polarized light transmittance of the Brewster thin-film polarizer 17, the transmittance transitions from the minimum value to the maximum value (the region from the wavelength $\lambda_4$ to the wavelength $\lambda_3$), that is, $\lambda_4 \leq \lambda_1 < \lambda_2 \leq \lambda_3$ be satisfied.

A difference $\Delta \lambda$ between the first wavelength $\lambda_1$ and the second wavelength $\lambda_2$ is preferably less than 45 nm, more preferably 40 nm or less, and further preferably 30 nm or less. Oscillation is enabled at a wavelength having a gain higher than that enabled by the related art, by setting the wavelength difference $\Delta \lambda$ to less than 45 nm.

Figure 3:
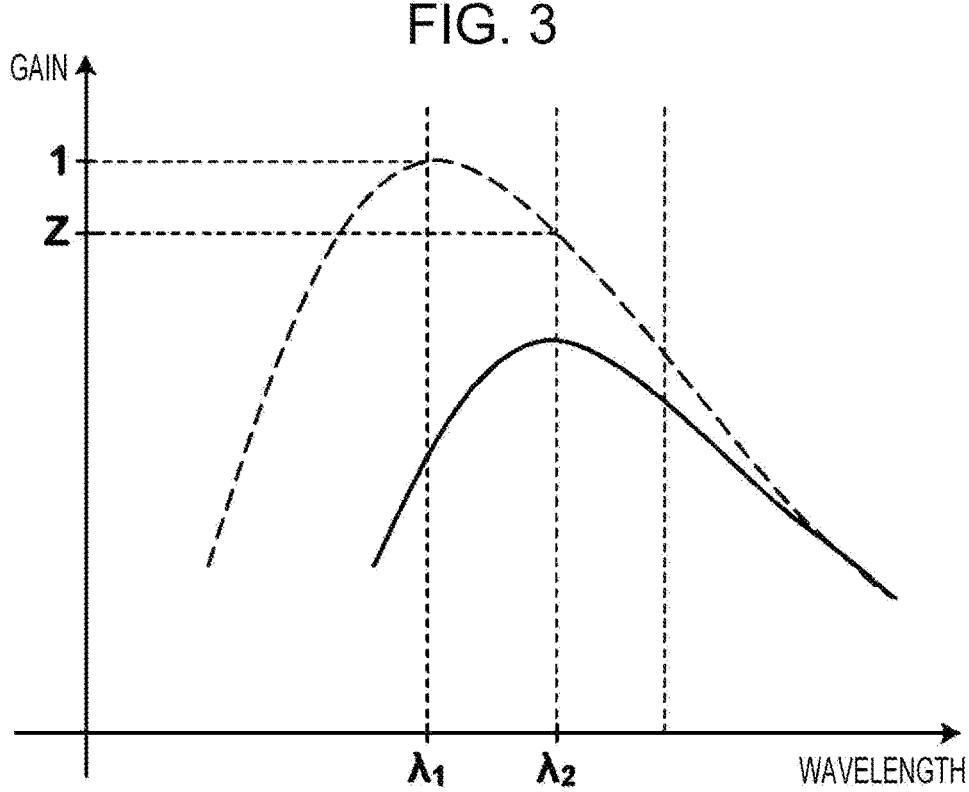
FIG. 3 is a schematic view of a gain curve of alexandrite and a gain curve in a case in which the thin-film polarizer illustrated in FIG. 2 is included in the laser device.

FIG. 3 schematically illustrates the wavelength characteristic of the gain of alexandrite crystal. In FIG. 3, the dashed line is the gain curve of alexandrite crystal. In contrast, the solid line is the effective gain curve when the laser device 10 includes the thin-film polarizer 17 having the wavelength selectivity illustrated in FIG. 2. As illustrated in FIG. 3, the gain of the alexandrite crystal is maximized at the first wavelength $\lambda_1$ (here, 755 nm) and decreases with distance from the first wavelength $\lambda_1$. Therefore, a small difference between the first wavelength $\lambda_1$ and the second wavelength $\lambda_2$ means that oscillation is enabled at a wavelength having a higher gain.

Here, when the gain (maximum gain) at the first wavelength $\lambda 1$ of the laser crystal is 1, the gain at the second wavelength $\lambda 2$ of the laser crystal is Z, the p-polarized light transmittance at the first wavelength $\lambda 1$ of the thin-film polarizer 17 is X, and the p-polarized light transmittance at the second wavelength $\lambda 2$ of the thin-film polarizer 17 is Y, $$1 \times X^2 < Z \times Y^2$$

is satisfied by X, Y, and Z. When the above expression is satisfied, oscillation at the second wavelength $\lambda_2$ is more dominant than oscillation at the first wavelength $\lambda_1$, and laser oscillation is performed at the second wavelength $\lambda_2$. Paradoxically, when oscillation is performed at the second wavelength $\lambda_2$ that is not a wavelength having the maximum gain, the above expression is considered to be satisfied regarding the second wavelength $\lambda_2$.

When the maximum gain of the laser crystal is 1, the gain Z at the second wavelength $\lambda_2$ of the laser crystal is preferably 0.7 or more. This is because higher laser output can be obtained by a higher gain at the second wavelength $\lambda_2$.

Although the gain curve is temperature dependent, here, the above-described gains at the first wavelength and the second wavelength are gains at a constant temperature.

In the present embodiment, the first wavelength is 755 nm, and the second wavelength is 780 nm. As illustrated in FIG. 2, in the laser device 10, due to inclusion of the Brewster thin-film polarizer 17 exhibiting the maximum value of transmittance at a wavelength near 780 nm, the gain at a wavelength less than 780 nm decreases considerably because most of the light at wavelengths less than 780 nm is reflected by the thin-film polarizer 17 and lost to the outside of the resonator. Specifically, as illustrated in FIG. 3, the gain curve of the alexandrite crystal, which exhibits the maximum gain at a wavelength of 755 nm, provides an effective gain curve in which the maximum gain is at a wavelength of 780 nm. As described above, the effective gain in the laser device 10 becomes maximized at a wavelength of 780 nm; thus, laser oscillation can be performed at such a wavelength of 780 nm.

Figure 9:
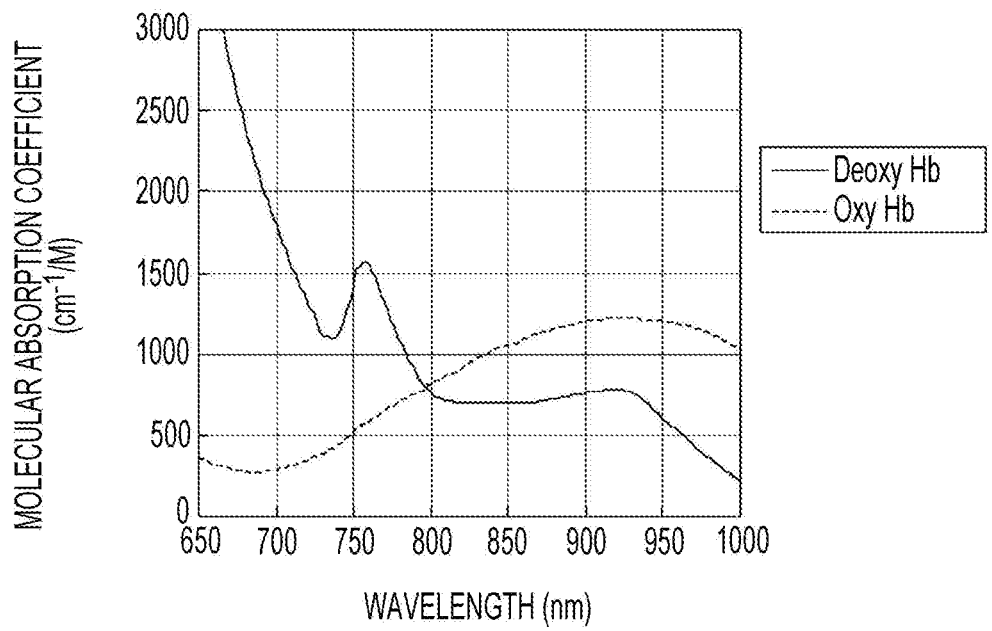
FIG. 9 illustrates wavelength characteristics exhibited by molecular absorption coefficients of oxidized hemoglobin and reduced hemoglobin.
Figure 10:
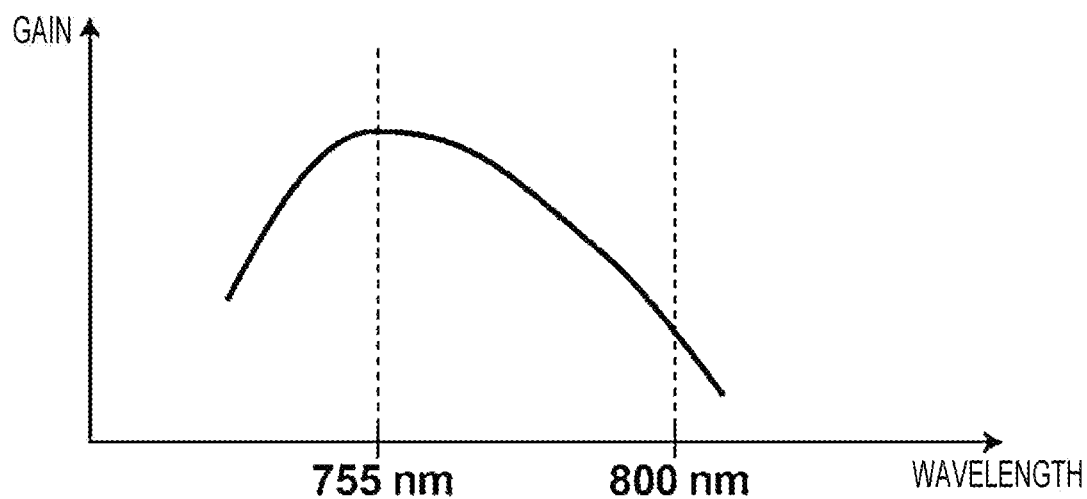
FIG. 10 is a schematic view of a gain curve of the alexandrite crystal.

In the above-described embodiment, a case in which the laser device 10 oscillates laser light at a wavelength of 780 nm as the second wavelength is described. However, the oscillation wavelength is not limited to 780 nm. For example, when the laser device 10 is used for a photoacoustic measurement apparatus, the wavelength of laser light, that is, the second wavelength is determined as appropriate in accordance with the optical absorption property of an absorber in a subject to be measured. In addition, for example, when a subject to be measured is hemoglobin in a living body (that is, when an image of a blood vessel is picked up), usually, a wavelength in this case is preferably a wavelength in a near-infrared wavelength range. The near-infrared wavelength range means a wavelength range from about 700 nm to about 850 nm. As illustrated in FIG. 9, oxidized hemoglobin and reduced hemoglobin differ from each other in terms of the wavelength characteristic of the molecular absorption coefficient. To detect blood vessels without distinguishing between a vein and an artery, it is preferable to use laser light at a wavelength near 800 nm, at which the molecular absorption coefficients of both blood vessels are equivalent to each other. However, as described above, there is a problem that, in alexandrite crystal, the gain at a wavelength of 800 nm is considerably low, laser output is low, and the S/N ratio of an obtainable image is low. In the present embodiment, by using laser light at a wavelength of 780 nm, it is possible to detect a photoacoustic wave in the region in which the signal difference between an artery and a vein is small and the gain of alexandrite crystal is not as low as that in the case of a wavelength of 800 nm. Thus, a blood vessel image with a satisfactory S/N ratio is obtainable. The second wavelength may be selected as appropriate in a range of ±10 nm, that is, in a range of 770 nm or more to 790 nm or less. If the wavelength difference Δλ of the second wavelength with respect to the first wavelength of 750 nm is 20 nm or more, it is possible to detect a photoacoustic wave in the range in which the difference between luminance of a vein and luminance of an artery is relatively small. Thus, such a condition is preferable.

Figure 4:
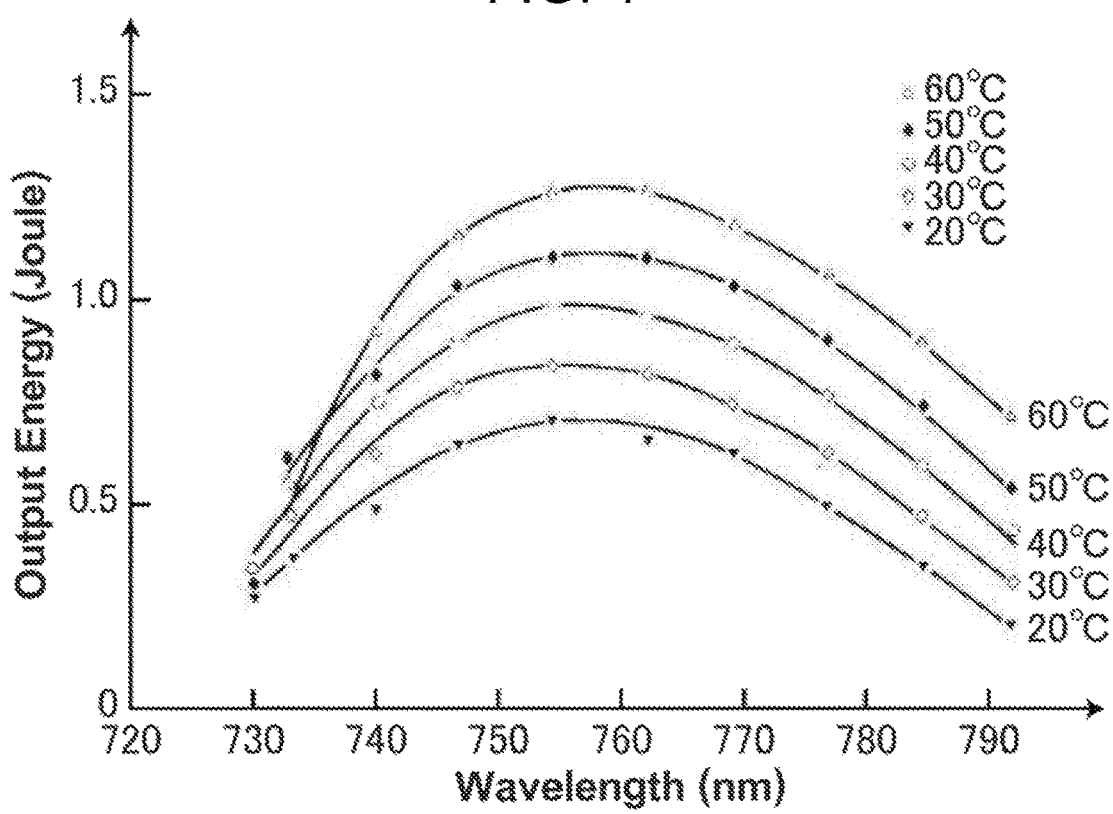
FIG. 4 illustrates gain curves of alexandrite crystal.

Here, regarding alexandrite crystal, the gain curves obtained by experiment are illustrated in FIG. 4. FIG. 4 illustrates the gain curves illustrated in John C. Walling, et al. "Tunable Alexandrite Lasers: Development and Performance", IEEE Journal of Quantum Electronics Vol. QE-21, No. 10, October 1985. As illustrated in FIG. 4, the gain curves change in accordance with temperature. When alexandrite crystal is used, the gain increases as temperature increases, and a wavelength exhibiting the maximum gain is in a range of 755 nm±5 nm.

Although the case in which alexandrite crystal is used as a laser crystal is described in the above-described embodiment, the laser crystal that is used in the laser device of the present invention is not limited to alexandrite crystal. For example, Ti:sapphire crystal may be used.

Figure 5:
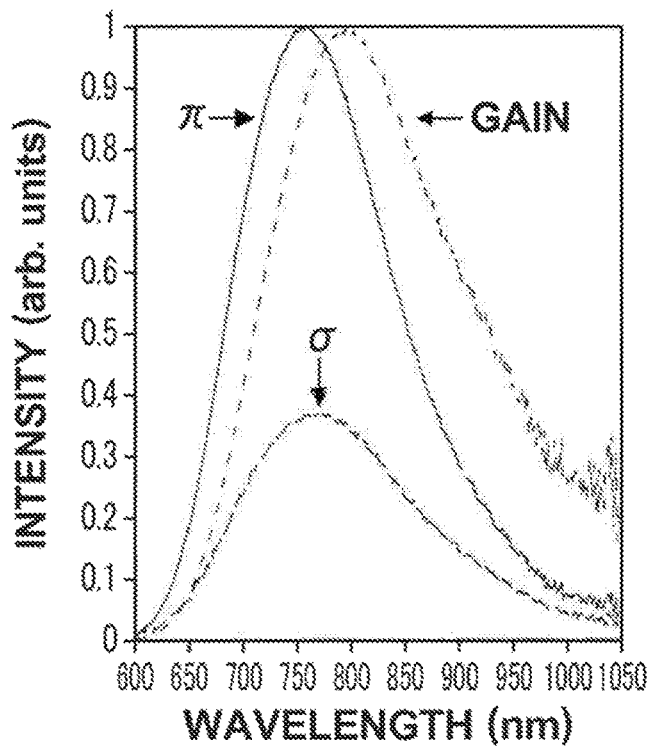
FIG. 5 illustrates gain curves of Ti:sapphire crystal.

Regarding Ti:sapphire crystal, the gain curve obtained by experiment is illustrated in FIG. 5. FIG. 5 illustrates the gain curve that is illustrated in P. F. Moulton, et al. "Spectroscopic and laser characteristics of Ti:Al$_2$O$_3$", Journal of the Optical Society of America B, Vol. 3, Issue 1, pp. 125-133 (1986). The gain curve is illustrated by the dashed line and denoted as GAIN in FIG. 5. The curved line denoted as π illustrates the emission spectrum of p-polarized light, and the curved line denoted as σ illustrates the emission spectrum of s-polarized light.

As illustrated in FIG. 5, Ti:sapphire exhibits a gain curve that is relatively broad as with alexandrite. Regarding Ti:sapphire, the gain is the highest and oscillation is preferentially performed at a wavelength near 800 nm, and the gain on the long-wavelength side is also relatively high. Therefore, laser oscillation at a wavelength of 835 nm can be performed by, for example, using a Brewster thin-film polarizer having the maximum value of the p-polarized light transmittance at a wavelength near 835 nm. In FIG. 2, it is possible to read $\lambda_1$ as 800 nm and $\lambda_2$ as 835 nm instead, and the relation between the wavelength characteristic of the p-polarized light transmittance of a Brewster polarizer used when Ti:sapphire is used and the first wavelength and the relation between the wavelength characteristic and the second wavelength are similar to those when alexandrite is used. In Ti:sapphire, the first wavelength exhibiting the maximum gain is preferably selected in a range of 800 nm±5 nm, and the second wavelength is preferably selected in a range of 835 nm±10 nm.

The difference between a laser device of the related art and the laser device of the present invention will be described. In a laser device, when pulse oscillation of laser light is performed, the phase of the light is shifted by half a wavelength by a Q switch (Pockels cell), a low Q value state is generated by a polarizer causing the shifted laser light to be lost to the outside of a resonator, and oscillation is then performed with an increased Q value. Such a polarizer is required to have a sufficiently high extinction ratio (the ratio between p-polarized light and s-polarized light in transmitted light). JP2015-111660A discloses a configuration in which a non-coated Brewster polarizer or a Brewster polarizer that includes a separation film that separates polarized light may be included to prevent an antireflection coating of a Q switch and a laser rod from being damaged. In contrast, in the present embodiment, a Brewster thin-film polarizer is used for wavelength selection to oscillate at a wavelength different from the maximum gain wavelength of the laser crystal. Thus, the purpose of use of a Brewster thin-film polarizer apparently differs between JP2015-111660A and the present embodiment. JP2015-111660A does not mention an oscillation wavelength at all and does not describe the availability of a Brewster thin-film polarizer for wavelength control of an oscillation wavelength.

In contrast, in a laser device, to oscillate laser light at a wavelength different from the maximum gain wavelength, a wavelength selection element for wavelength selection is usually provided in a resonator as described in JP2013-089680A, JP2013-214703A, and JP2015-191918A. In the laser devices of JP2013-089680A, JP2013-214703A, and JP2015-191918A, for example, as a wavelength selection element, a reflection member having wavelength selectivity is used for a mirror, or a wavelength selective filter such as a band-pass filter or a long-pass filter is included. In contrast, in the laser device of the present embodiment, other than the Brewster thin-film polarizer, an optical element having wavelength selectivity is not included.

A usual wavelength selective filter such as a band-pass filter or a long-pass filter has a wide transition wavelength region of 50 nm or more in which transmittance changes from the maximum transmittance to the minimum transmittance in the wavelength characteristic of transmittance. Therefore, when oscillation is attempted at a wavelength longer than the maximum gain wavelength, oscillation is only enabled at a wavelength of at least 45 nm or longer than the maximum gain wavelength or at a wavelength of at least 45 nm or shorter than the maximum gain wavelength. For manufacturing a wavelength selective filter having a transition wavelength region of 50 nm or less, a complex optical film design is required, and not only costs increase but also risks of optical film damage due to multilayering of the optical film increase.

The laser device of the present invention, as described above, includes the laser crystal, the resonator including the pair of mirrors between which the laser crystal is interposed, the Q switch that is disposed on the optical path of the resonator and controls the Q value of the resonator, and the Brewster thin-film polarizer that is disposed on the optical path of the resonator and transmits selectively the p-polarized light. The thin-film polarizer has wavelength selectivity in which the p-polarized light transmittance at the first wavelength exhibiting the maximum gain of the laser crystal is 5% or more to 25% or less, the p-polarized light transmittance monotonically increases as a wavelength becomes longer than the first wavelength, and the maximum transmittance is exhibited at the third wavelength. The laser device of the present invention oscillates laser light at the second wavelength that is a wavelength longer than the first wavelength and shorter than or equal to the third wavelength and that has a p-polarized light transmittance of 90% or more in the thin-film polarizer.

The Brewster thin-film polarizer has a considerably narrow transition wavelength width from the minimum value to the maximum value of the p-polarized light transmittance and exhibits an abrupt change in the p-polarized light transmittance compared with wavelength selective filters such as a band-pass filter and a long-pass filter. Therefore, as the second wavelength that is an oscillation wavelength, it is possible to select a wavelength closer to the first wavelength exhibiting the maximum gain, that is, a wavelength exhibiting a higher gain compared with a case in which a laser device of the related art is used. For example, when the alexandrite crystal is used as a laser crystal, the second wavelength is enabled to be 780 nm, and oscillation with a larger gain can be performed compared with when light at a wavelength of 800 nm is oscillated as laser light at a wavelength different from the maximum gain wavelength as with the laser devices of JP2013-089680A, JP2013-214703A, and JP2015-191918A. The gain is large compared with the case of a wavelength of 800 nm; thus, it is possible to reduce the amount of supplied power and suppress an increase in the size of devices and an increase in costs. In addition, when oscillation is performed with the same amount of supplied power, it is possible to generate a laser output larger than that of a wavelength of 800 nm and to suppress a decrease in output.

Multi-Wavelength Laser Device

Figure 6:
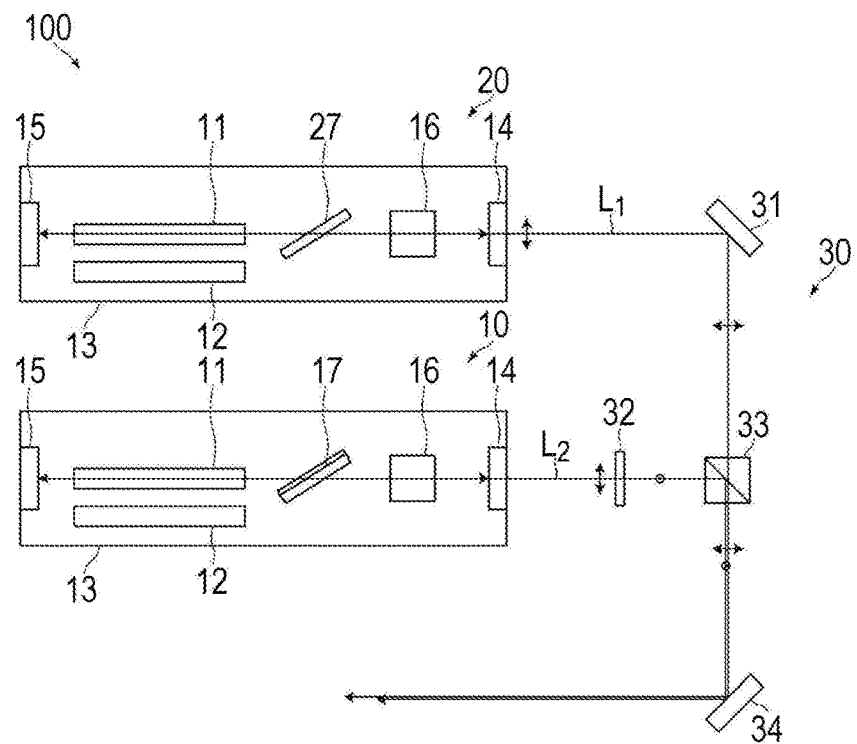
FIG. 6 is a schematic view of a configuration of a multi-wavelength laser device of an embodiment of the present invention.

FIG. 6 is a schematic view of a configuration of a multi-wavelength laser device according to an embodiment of the present invention A multi-wavelength laser device 100 includes a first laser unit 20 that oscillates first laser light $L_1$ at a first wavelength, a second laser unit 10 that oscillates second laser light $L_2$ at a second wavelength that is a wavelength longer than the first wavelength, and a wave-combining unit 30 that causes the optical path of the first laser light $L_1$ output from the first laser unit 20 and the optical path of the second laser light $L_2$ output from the second laser unit 10 to coincide with each other.

The second laser unit 10 is the laser device 10 of the above-described embodiment of the present invention. That is, the second laser unit 10 has the laser rod 11, the flash lamp 12, the laser chamber 13, the pair of mirrors 14 and 15, the Q switch 16, and the Brewster thin-film polarizer 17. The second laser unit 10 oscillates laser light at the second wavelength (the second laser light $L_2$) that is longer than the first wavelength exhibiting the maximum gain of a laser crystal. The gain at the second wavelength is smaller than that at the first wavelength. Details of each component are described above.

The first laser unit 20 is a laser device that has the same configuration as the second laser unit 10 and that includes a non-coated Brewster polarizer 27 instead of the Brewster thin-film polarizer 17. That is, the first laser unit 20 has the laser rod 11, the flash lamp 12, the laser chamber 13, the pair of mirrors 14 and 15, the Q switch 16, and the Brewster polarizer 27. The first laser unit 20 oscillates laser light at the first wavelength (the first laser light $L_1$) exhibiting the maximum gain of the laser crystal.

In each of the laser units 10 and 20, alexandrite crystal is used as the laser rod 11, and the wavelength of the first laser light $L_1$ is 755 nm and the wavelength of the second laser light $L_2$ is 780 nm.

The Brewster polarizer 27 is a non-coated glass plate that is made of a material such as silica glass or borosilicate glass and that is disposed at a Brewster's angle. "Non-coated" means that a film that can be damaged by light having high energy density is not provided at the very least, such as a film for separating p-polarized light and s-polarized light from each other, an antireflection film, or a protection film, and it is not required that any films are not provided.

The polarizer 27 is a non-coated polarizer as described above and does not have wavelength selectivity. Thus, the first laser unit 20 oscillates light at the first wavelength that exhibits the maximum gain of the laser rod 11.

The wave-combining unit 30 includes a mirror 31 that reflects the first laser light $L_1$ output from the first laser unit 20, a half-wave plate 32 that is disposed on the optical path of the second laser light $L_2$ output from the second laser unit 10, a polarization beam splitter 33 that transmits the first laser light $L_1$ and reflects the second laser light $L_2$, and a mirror 34 that reflects the first laser light $L_1$ and the second laser light $L_2$.

The mirror 31 is disposed so that the first laser light $L_1$ is to be incident at an incidence angle of 45°, shifts the optical path of the first laser light $L_1$ by 90°, and reflects the first laser light $L_1$ toward the polarization beam splitter 33.

The half-wave plate 32 shifts the phase of laser light emitted from the second laser unit 10 by half a wavelength and converts the polarized light of the laser light to polarized light orthogonal to the original polarized light. Laser light emitted from the first laser unit 20 and the second laser unit 10 is p-polarized light. The second laser light $L_2$ passes through the half-wave plate 32, becomes s-polarized light, and is reflected by the polarization beam splitter 33. The half-wave plate can be omitted from the second laser unit 10 by arranging the laser rod 11 and the Brewster thin-film polarizer 17 at positions rotated by 90° with respect to the laser rod 11 and the Brewster thin-film polarizer 17 of the first laser unit 20. That is, if the laser rods and the polarizers in the first and second laser units 20 and 10 are arranged so that polarization directions of the first laser light $L_1$ output from the first laser unit 20 and the second laser light $L_2$ output from the second laser unit 10 are orthogonal to each other, the half-wave plate is not required.

The polarization beam splitter 33 reflects the s-polarized light and transmits the p-polarized light. Therefore, the polarization beam splitter 33 transmits the first laser light $L_1$ and reflects the second laser light $L_2$ that has passed through the half-wave plate and has become the s-polarized light. Due to the function of the polarization beam splitter 33, the first laser light and the second laser light are to be output on the same optical path.

The mirror 34 is disposed on the optical path of the first laser light that has passed through the polarization beam splitter 33 and on the optical path of the second laser light that has been reflected by the polarization beam splitter 33 so that the first laser light $L_1$ and the second laser light $L_2$ are to be incident at an incidence angle of 45°, and the mirror 34 reflects both laser light.

With the above-described configuration, the multi-wavelength laser device 100 of the present embodiment can emit the first laser light $L_1$ at a wavelength of 755 nm and the second laser light $L_2$ at a wavelength of 780 nm alternately or simultaneously.

In the dual-wavelength laser devices disclosed in JP2013-089680A, JP2013-214703A, and JP2015-191918A, dual wavelengths of 755 nm, which is the maximum gain wavelength, and 800 nm are used when alexandrite crystal is used. As described above, the gain at a wavelength of 800 nm is considerably smaller than the maximum gain in the alexandrite crystal. In the present embodiment, it is possible to suppress a decrease in gain and a decrease in output compared with the case in which light at a wavelength of 800 nm is oscillated because a wavelength of 780 nm is used as the second wavelength.

The multi-wavelength laser device 100 of the present embodiment is preferably used, for example, for a photoacoustic measurement apparatus. With reference to FIG. 9 described above, the molecular absorption coefficient of oxygenated hemoglobin, which is included abundantly in human arteries, at a wavelength of 755 nm is lower than the molecular absorption coefficient thereof at a wavelength of 780 nm. In contrast, the molecular absorption coefficient of reduced hemoglobin, which is included abundantly in veins, at a wavelength of 755 nm is higher than the molecular absorption coefficient thereof at a wavelength of 780 nm. By utilizing such characteristics, it is possible to distinguish between a photoacoustic signal from an artery and a photoacoustic signal from a vein in such a manner that a photoacoustic signal obtained at a wavelength of 755 nm is assessed and determined to be relatively small or large with respect to a photoacoustic signal obtained at a wavelength of 780 nm. Alternatively, oxygen saturation can be measured. Theoretically, any combination of dual wavelengths is possible provided that there is a difference between the light absorption coefficients of the two selected wavelengths, and the combination is not limited to the above-described combination of 755 nm and 800 nm.

For example, the first wavelength of Ti:sapphire exhibiting the maximum gain is 800 nm. As described above, when the laser device is applied to a photoacoustic measurement apparatus and an image of blood vessels is picked up without distinguishing between an artery and a vein, it is preferable that laser light at a wavelength near 800 nm be used. Thus, it is also preferable that Ti:sapphire instead of alexandrite be included as a laser medium in the laser units 10 and 20. For example, the multi-wavelength laser device in FIG. 6 is configured to include Ti:sapphire crystal as a laser rod and include, as a Brewster thin-film polarizer, a thin-film polarizer that has the maximum value of p-polarized light transmittance at a wavelength near 835 nm. Due to the configuration, it is possible to cause the second laser unit including the Brewster thin-film polarizer to output laser light at the second wavelength near 835 nm and, for example, to cause the laser unit including a non-coated Brewster polarizer to output the first laser light at the first wavelength of 800 nm. In this case, it is also possible to obtain effects similar to those when alexandrite crystal is used.

Although, in the above case, as a multi-wavelength laser device, the configuration in which the first laser device and the second laser device are arranged in parallel is described, a multi-wavelength laser device can also be realized by providing a single resonator and by including a polarizer exchange mechanism capable of exchanging a Brewster thin-film polarizer and a non-coated Brewster polarizer in the resonator. In this case, by exchanging the polarizers on the optical path of the resonator, the laser device can selectively oscillate at the first wavelength or at the second wavelength according to a disposed polarizer.

Photoacoustic Measurement Apparatus According to First Embodiment

Figure 7:
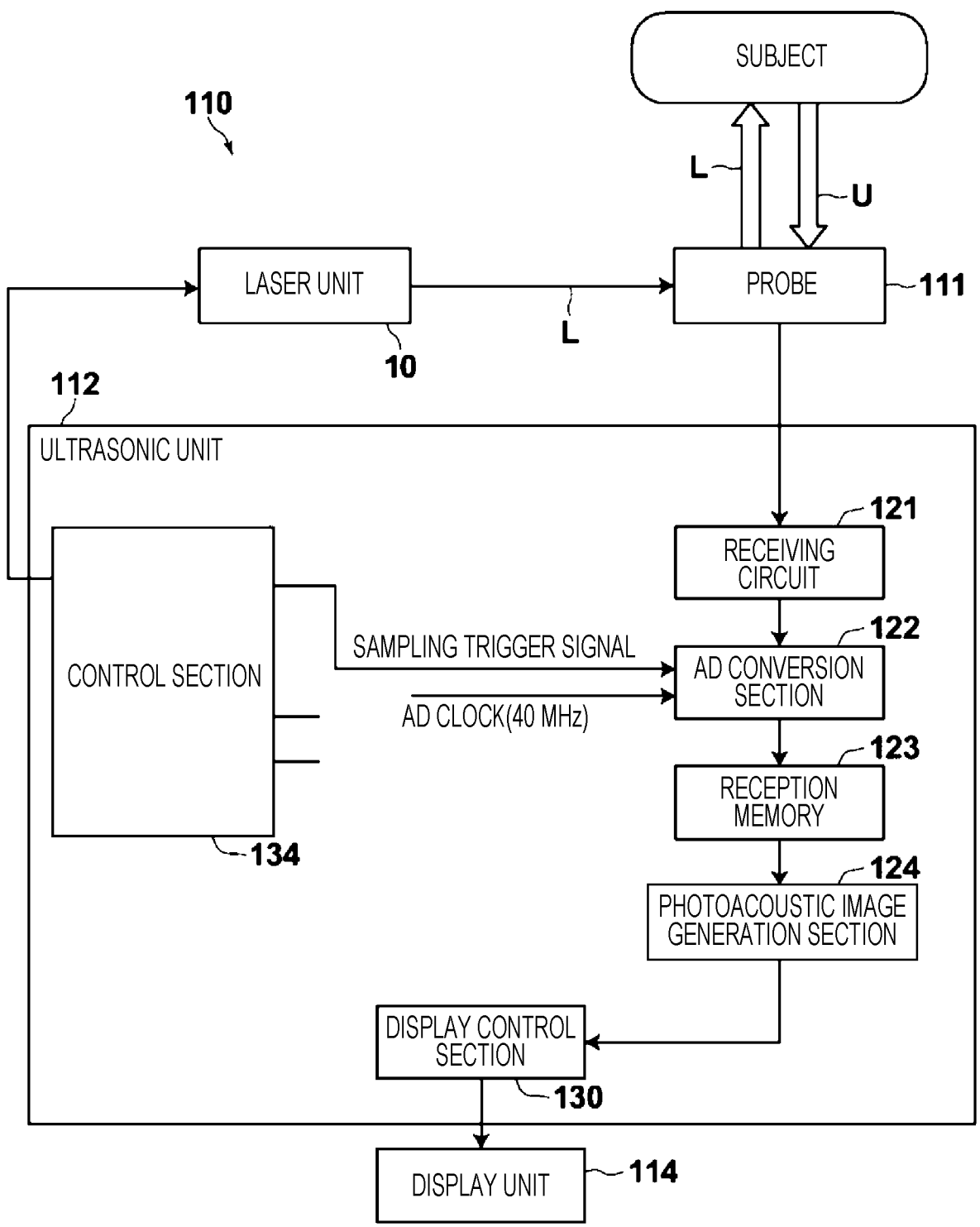
FIG. 7 is a block diagram of a photoacoustic measurement apparatus of a first embodiment including a laser device.

A photoacoustic measurement apparatus including the laser device of the first embodiment will be described. FIG. 7 is a block diagram of a configuration of the photoacoustic measurement apparatus of the present embodiment.

A photoacoustic measurement apparatus 110 of the present embodiment has a photoacoustic image generation function that generates a photoacoustic image based on, for example, a photoacoustic signal. As illustrated in FIG. 7, the photoacoustic measurement apparatus 110 of the present embodiment includes an ultrasonic probe (a probe) 111, an ultrasonic unit 112, and a laser unit that is the laser device 10 of an embodiment illustrated in FIG. 1 (hereinafter, referred to as a laser unit 10), and a display unit 114. The laser unit 10 emits pulsed laser light with which a subject is irradiated.

The laser unit 10 is the above-described laser device 10 and, as laser light, outputs laser light at the second wavelength longer than the maximum gain wavelength of alexandrite crystal forming the laser rod 11 as measurement light L. Here, laser light at a wavelength of 780 nm is output. The laser unit 10 is configured, for example, to output laser light by receiving a trigger signal from a control section 134 of the ultrasonic unit 112. The laser unit 10 preferably outputs pulsed light having a pulse width of 1 nsec to 100 nsec as laser light. The laser light that has been output from the laser unit 10 is guided to the probe 111 by light guide means such as an optical fiber, and the subject is irradiated with the laser light from the probe 111. Irradiation with laser light may be performed from a location other than the probe 111. In the subject, an ultrasonic wave (acoustic wave) U is generated by a light absorber absorbing the energy of the irradiated laser light.

The probe 111 is a photoacoustic wave detection unit that detects a photoacoustic wave that is generated in the subject by the absorber in the subject absorbing laser light. For example, the probe 111 has a plurality of ultrasonic detector elements (ultrasonic transducers) that are arranged one-dimensionally and detects acoustic waves (photoacoustic signals) from the inside of the subject by the ultrasonic transducers arranged one-dimensionally.

The ultrasonic unit 112 has a receiving circuit 121, an AD conversion section 122, a reception memory 123, a photoacoustic image generation section 124, a display control section 130, and the control section 134.

The control section 134 controls each unit of the photoacoustic measurement apparatus 110 and, in the present embodiment, includes a trigger control circuit (not illustrated). The trigger control circuit, for example, sends a light trigger signal to the laser unit 10 on starting the photoacoustic measurement apparatus 110. Therefore, in the laser unit 10, the flash lamp is lit, and the excitation of the laser rod is started. The excited state of the laser rod is maintained, and the laser unit 10 becomes capable of outputting pulsed laser light.

The control section 134 then sends a Qsw trigger signal from the trigger control circuit to the laser unit 10. That is, the control section 134 controls the output timing of the pulsed laser light from the laser unit 10 by using the Qsw trigger signal. In addition, in the present embodiment, when sending the Qsw trigger signal, the control section 134 simultaneously sends a sampling trigger signal to the AD conversion section 122. The sampling trigger signal is to be a cue of the start timing of the sampling of the photoacoustic signal in the AD conversion section 122. Therefore, the photoacoustic signal can be sampled in synchronization with the output of the laser light by using the sampling trigger signal.

The receiving circuit 121 receives the photoacoustic signal that has been detected by the probe 111. The photoacoustic signal that has been received by the receiving circuit 121 is sent to the AD conversion section 122.

The AD conversion section 122 samples the photoacoustic signal that has been received by the receiving circuit 121 and converts the photoacoustic signal to a digital signal. The AD conversion section 122, for example, samples the photoacoustic signal that has been received in a predetermined sampling period in synchronization with an AD clock signal, at a predetermined frequency, that is input from outside.

The reception memory 123 stores the photoacoustic signal that has been sampled by the AD conversion section 122. The reception memory 123 then outputs the data of the photoacoustic signal that has been detected by the probe 111 to the photoacoustic image generation section 124.

The photoacoustic image generation section 124, for example, reconstructs data per line by adding portions of the photoacoustic data that are stored in the reception memory 123 and that are obtained at delay times according to the respective positions of the ultrasonic transducers and generates the data of a tomographic image (photoacoustic image) based on the photoacoustic data of each line. The photoacoustic image generation section 124 may perform the reconstruction by using a circular back projection (CBP) method instead of the delay addition method. The photoacoustic image generation section 124 outputs the data of the photoacoustic image that has been generated as described above to the display control section 130.

The display control section 130 performs predetermined display processing with respect to the photoacoustic image data and causes the display unit 114 such as a display device to display a photoacoustic image based on the photoacoustic image data that has been subjected to the predetermined display processing. When a plurality of photoacoustic images are obtained by the probe 111 having a two-dimensionally arranged transducer array or by the probe 111 performing probe scanning, the display control section 130, for example, can also cause the display unit 114 to display a composite image as a three-dimensional image by generating volume data based on such photoacoustic images.

As described above, when a subject to be measured is hemoglobin in a living body (that is, when the image of a blood vessel is picked up), to detect the blood vessels without distinguishing between a vein and an artery, it is preferable to use laser light at a wavelength near 800 nm at which the molecular absorption coefficients of both types of blood vessels are equivalent to each other. However, there is a problem that, in alexandrite crystal, the gain at a wavelength of 800 nm is considerably low, laser output is low, and the S/N ratio of an obtainable image is low. In the present embodiment, by using laser light at a wavelength of 780 nm, it is possible to detect a photoacoustic wave in the range in which the signal difference between a vein and an artery is small and the gain of the alexandrite crystal is not as low as that in the case of a wavelength of 800 nm. Thus, a blood vessel image with a satisfactory S/N ratio is obtainable.

Photoacoustic Measurement Apparatus According to Second Embodiment

Figure 8:
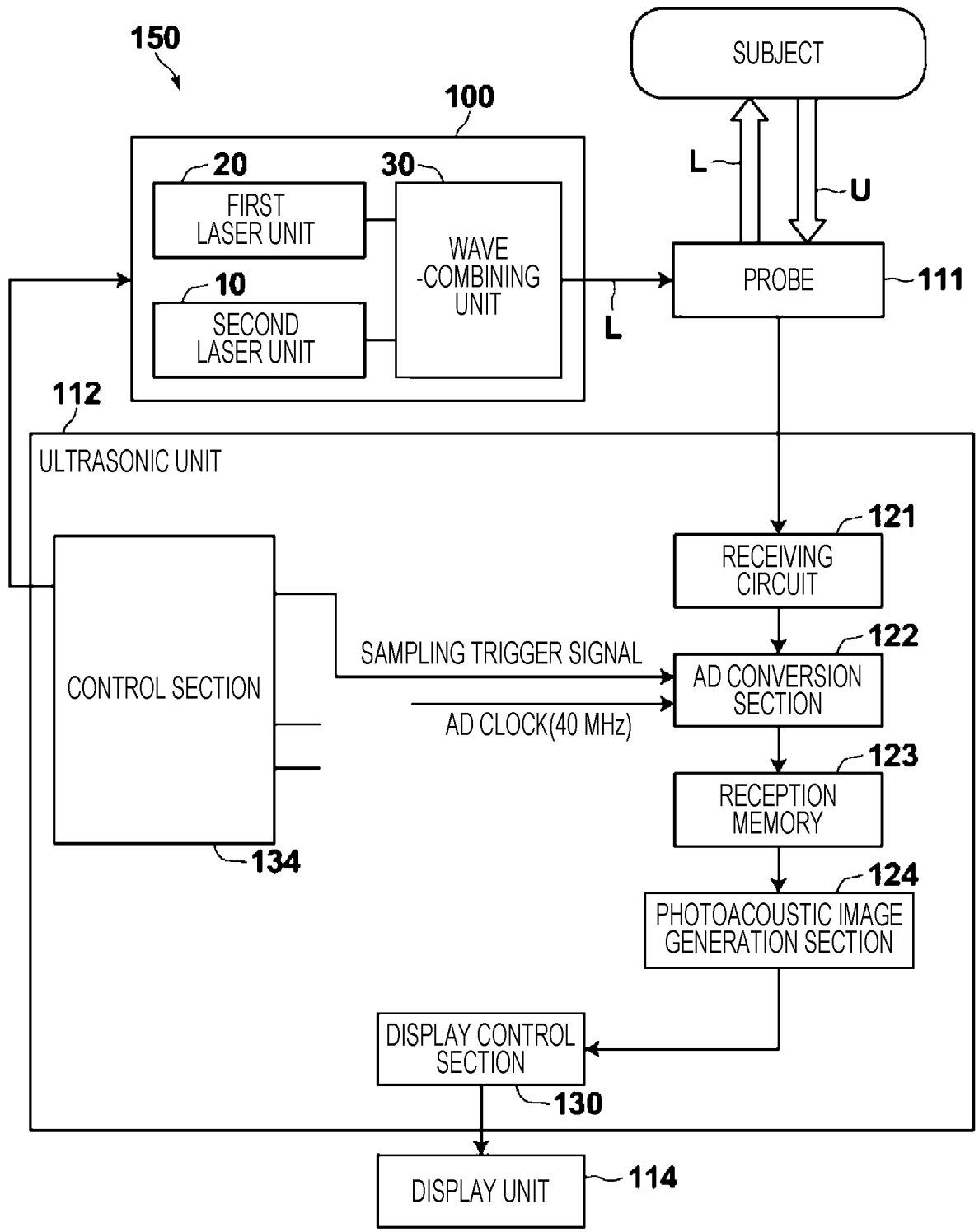
FIG. 8 is a block diagram of a photoacoustic measurement apparatus of a second embodiment including a multi-wavelength laser device.

An embodiment of a photoacoustic measurement apparatus according to a second embodiment will be described. FIG. 8 is a block diagram of a configuration of a photoacoustic measurement apparatus 150 of the present embodiment.

The photoacoustic measurement apparatus 150 of the present embodiment has, for example, a photoacoustic image generation function that generates a photoacoustic image based on a photoacoustic signal. As illustrated in FIG. 8, the photoacoustic measurement apparatus 150 of the present embodiment includes a probe 111, an ultrasonic unit 112, a laser light source unit that is the multi-wavelength laser device 100 of an embodiment illustrated in FIG. 6 (hereinafter, referred to as a laser light source unit 100), and a display unit 114. The laser light source unit 100 emits multi-wavelength pulsed laser light with which a subject is irradiated. The same components as those of the photoacoustic measurement apparatus 110 of the first embodiment illustrated in FIG. 7 are given the same references as those given for the photoacoustic measurement apparatus 110, the detailed description about the same functions will be omitted, and points of difference will be described in detail.

The laser light source unit 100 is the above-described multi-wavelength laser device 100 and includes the first laser unit 20, the second laser unit 10, and the wave-combining unit 30. The laser light source unit 100, as laser light, outputs laser light at a first wavelength (first laser light) that is the maximum gain wavelength of alexandrite crystal forming a laser rod and laser light at a second wavelength (second laser light) longer than the first wavelength as measurement light L. Here, the first wavelength is 755 nm, and the second wavelength is 780 nm.

Laser light that has been output from the laser light source unit 100 is guided to the probe 111 by light guide means such as an optical fiber, and a subject is irradiated with the laser light from the probe 111. The first laser light and the second laser light are emitted simultaneously or emitted alternately while being switched.

In the control section 134, a trigger control circuit first outputs a flash lamp trigger to cause the first laser unit 20 of the laser light source unit 100 to emit pulsed laser light at the first wavelength (755 nm). Therefore, in the first laser unit 20, the flash lamp is lit, an excited state of the laser rod is maintained, and the first laser unit 20 becomes capable of outputting pulsed laser light. A Qsw trigger signal is then sent from the trigger control circuit to the first laser unit 20. That is, the control section 134 controls the output timing of the pulsed laser light from the first laser unit 20 by using the Qsw trigger signal. Therefore, the laser light source unit 100 emits the first laser light.

The pulsed laser light at a wavelength of 800 nm that has been emitted from the laser light source unit 100 is guided, for example, to the probe 111, and the subject is irradiated with the pulsed laser light from the probe 111. In the subject, a photoacoustic signal is generated by a light absorber absorbing the energy of the irradiated pulsed laser light. The probe 111 detects the photoacoustic signal that has been generated in the subject. The photoacoustic signal that has been detected by the probe 111 is received by the receiving circuit 121.

The trigger control circuit outputs a sampling trigger to the AD conversion section 122 in synchronization with the timing of the Q switch. The AD conversion section 122 samples the photoacoustic signal that has been received by the receiving circuit 121 in a predetermined sampling period. The photoacoustic signal that has been sampled by the AD conversion section 122 is stored in the reception memory 123 as first photoacoustic data.

When the preparation for receiving the next photoacoustic signal is complete, the trigger control circuit outputs a flash lamp trigger to the second laser unit 10 of the laser light source unit 100 to cause the second laser unit 10 to emit the second laser light at the second wavelength (780 nm). Therefore, in the second laser unit 10, the flash lamp is lit, an excited state of the laser rod is maintained, and the second laser unit 10 becomes capable of outputting pulsed laser light. A Qsw trigger signal is then sent from the trigger control circuit to the laser unit 10. That is, the control section 134 controls the output timing of the pulsed laser light from the laser unit 10 by using the Qsw trigger signal. Therefore, the laser light source unit 100 emits the second laser light.

The trigger control circuit outputs a sampling trigger to the AD conversion section 122 in synchronization with the timing of the Q switch. The AD conversion section 122 samples the photoacoustic signal that has been received by the receiving circuit 121 in a predetermined sampling period. The photoacoustic signal that has been sampled by the AD conversion section 122 is stored in the reception memory 123 as second photoacoustic data.

The AD conversion section 122 causes photoacoustic data to be stored in the reception memory 123. The AD conversion section 122 causes photoacoustic data corresponding to each wavelength of pulsed laser light emitted from the laser light source unit 100 to be stored in the reception memory 123. That is, the AD conversion section 122 causes the first photoacoustic data in which photoacoustic signals detected by the probe 111 are sampled when the subject is irradiated with the first laser light at the first wavelength and the second photoacoustic data in which photoacoustic signals detected by the probe 111 are sampled when the subject is irradiated with the second laser light at the second wavelength, to be stored in the reception memory 123.

Based on the first photoacoustic data and the second photoacoustic data that are stored in the reception memory 123, the photoacoustic image generation section 124 generates intensity information indicating signal intensity based on the magnitude relation of relative signal intensities between photoacoustic data corresponding to the respective wavelengths and based on the photoacoustic data corresponding to the respective wavelengths. Based on such information, a photoacoustic image is generated.

Absorption of energy of pulsed laser light by oxidized hemoglobin is larger at a wavelength of 780 nm than at a wavelength of 755 nm. Absorption of energy of pulsed laser light by reduced hemoglobin is smaller at a wavelength of 780 nm than at a wavelength of 755 nm. Thus, an absorber can be identified as reduced hemoglobin or oxidized hemoglobin by comparing the first photoacoustic data with the second photoacoustic data. That is, each measured blood vessel can be identified as a vein in which blood containing mainly reduced hemoglobin flows or as an artery in which blood containing mainly oxidized hemoglobin flows. Therefore, for example, a color-coded photoacoustic image can be displayed on a display screen while veins and arteries are distinguished.

As described above, by including the multi-wavelength laser device 100 as a laser light source unit, functional imaging utilizing a difference of the optical absorption property of each optical absorber according to a wavelength can be performed by irradiating the subject with pulsed laser light at a plurality of wavelengths and by using a photoacoustic signal (photoacoustic data) that is detected when irradiation of pulsed laser light at each wavelength is performed.

In the multi-wavelength laser device 100 of the photoacoustic measurement apparatus according to the second embodiment, instead of alexandrite crystal, Ti:sapphire crystal may be used to form a laser rod. In this case, photoacoustic measurement can be performed with a wavelength of the first laser light as 800 nm and with a wavelength of the second laser light as 840 nm, and, as with when alexandrite is used, for example, a color-coded photoacoustic image can be displayed on the display screen while veins and arteries are distinguished.

Each of the photoacoustic measurement apparatuses 110 and 150 according to the first and second embodiments may have a configuration in which the probe 111 sends ultrasonic waves to a subject and a reflected acoustic wave image is generated based on signals of reflected waves of the acoustic waves that have been sent. A portion that cannot be imaged in the photoacoustic image can be observed by generating an ultrasonic image in addition to the photoacoustic image and by referring to the ultrasonic image.

The laser device or the multi-wavelength laser device of the present invention can also be used for an apparatus different from a photoacoustic measurement apparatus.

REFERENCE SIGNS LIST

10 laser device (second laser unit, laser unit)
11 laser rod
12 flash lamp
13 laser chamber
14, 15 mirror constituting resonator
16 Q switch
17 Brewster thin-film polarizer
17a glass plate
17b thin film
20 first laser unit
27 non-coated Brewster polarizer
30 wave-combining unit
31, 34 mirror
32 half-wave plate
33 polarization beam splitter
100 multi-wavelength laser device (laser light source unit)
110, 150 photoacoustic measurement apparatus
111 probe
112 ultrasonic unit
114 display unit
121 receiving circuit
122 conversion section
123 reception memory
124 photoacoustic image generation section
130 display control section
134 control section
$L_1$ first laser light
$L_2$ second laser light

What is claimed is:

1. A multi-wavelength laser device, comprising:
a first laser unit that oscillates first laser light at a first wavelength;
a second laser unit that oscillates second laser light at a second wavelength that is a wavelength longer than the first wavelength; and
a wave-combining unit that causes an optical path of the first laser light output from the first laser unit and an optical path of the second laser light output from the second laser unit to coincide with each other, wherein:
the second laser unit is laser device comprising:
a laser crystal;
a resonator including a pair of mirrors between which the laser crystal is interposed;
a Q switch that is disposed on an optical path of the resonator and controls a Q value of the resonator; and
a Brewster thin-film polarizer that is disposed on the optical path of the resonator and transmits selectively p-polarized light,
wherein the thin-film polarizer has wavelength selectivity in which a p-polarized light transmittance at a first wavelength exhibiting a maximum gain of the laser crystal is 5% or more to 25% or less, the p-polarized light transmittance monotonically increases as a wavelength becomes longer than the first wavelength, and a maximum transmittance is exhibited at a third wavelength, and
wherein the laser device oscillates laser light at a second wavelength that is a wavelength longer than the first wavelength and shorter than or equal to the third wavelength and that has a p-polarized light transmittance of 90% or more in the thin-film polarizer, and
the first laser unit is a laser device that has the same configuration as the second laser unit and that comprises a non-coated Brewster polarizer instead of the Brewster thin-film polarizer.

2. The multi-wavelength laser device according to claim 1,
wherein the p-polarized light transmittance of the thin-film polarizer is 20% or less at the first wavelength and 95% or more at the second wavelength.

3. The multi-wavelength laser device according to claim 2,
wherein a difference in wavelength between the first wavelength and the second wavelength is less than 45 nm.

4. The multi-wavelength laser device according to claim 3,
wherein the difference in wavelength between the first wavelength and the second wavelength is 40 nm or less.

5. The multi-wavelength laser device according to claim 4,
wherein, when a gain at the first wavelength of the laser crystal is 1, a gain at the second wavelength of the laser crystal is Z,
the p-polarized light transmittance at the first wavelength of the thin-film polarizer is X, and the p-polarized light transmittance at the second wavelength of the thin-film polarizer is Y,
$$1 \times X^2 < Z \times Y^2$$
is satisfied.

6. The multi-wavelength laser device according to claim 3,
wherein, when a gain at the first wavelength of the laser crystal is 1, a gain at the second wavelength of the laser crystal is Z,
the p-polarized light transmittance at the first wavelength of the thin-film polarizer is X, and the p-polarized light transmittance at the second wavelength of the thin-film polarizer is Y,
$$1 \times X^2 < Z \times Y^2$$
is satisfied.

7. The multi-wavelength laser device according to claim 2,
wherein, when a gain at the first wavelength of the laser crystal is 1, a gain at the second wavelength of the laser crystal is Z,
the p-polarized light transmittance at the first wavelength of the thin-film polarizer is X, and the p-polarized light transmittance at the second wavelength of the thin-film polarizer is Y,
$$1 \times X^2 < Z \times Y^2$$
is satisfied.

8. The multi-wavelength laser device according to claim 1,
wherein a difference in wavelength between the first wavelength and the second wavelength is less than 45 nm.

9. The multi-wavelength laser device according to claim 8,
wherein the difference in wavelength between the first wavelength and the second wavelength is 40 nm or less.

10. The multi-wavelength laser device according to claim 9,
wherein, when a gain at the first wavelength of the laser crystal is 1, a gain at the second wavelength of the laser crystal is Z,
the p-polarized light transmittance at the first wavelength of the thin-film polarizer is X, and the p-polarized light transmittance at the second wavelength of the thin-film polarizer is Y, $$1 \times X^2 < Z \times Y^2$$

is satisfied.

11. The multi-wavelength laser device according to claim 8,
wherein, when a gain at the first wavelength of the laser crystal is 1, a gain at the second wavelength of the laser crystal is Z,
the p-polarized light transmittance at the first wavelength of the thin-film polarizer is X, and the p-polarized light transmittance at the second wavelength of the thin-film polarizer is Y, $$1 \times X^2 < Z \times Y^2$$

is satisfied.

12. The multi-wavelength laser device according to claim 1,
wherein, when a gain at the first wavelength of the laser crystal is 1, a gain at the second wavelength of the laser crystal is Z,
the p-polarized light transmittance at the first wavelength of the thin-film polarizer is X, and the p-polarized light transmittance at the second wavelength of the thin-film polarizer is Y, $$1 \times X^2 < Z \times Y^2$$

is satisfied.

13. The multi-wavelength laser device according to claim 1,
wherein, when the maximum gain of the laser crystal is 1, a gain at the second wavelength of the laser crystal is 0.7 or more.

14. The multi-wavelength laser device according to claim 1,
wherein the first wavelength is 755 nm±5 nm, and the second wavelength is 780 nm±10 nm.

15. The multi-wavelength laser device according to claim 14,
wherein the laser crystal is alexandrite crystal.

16. The multi-wavelength laser device according to claim 1,
wherein the first wavelength is 800 nm±5 nm, and the second wavelength is 835 nm±10 nm.

17. The multi-wavelength laser device according to claim 16,
wherein the laser crystal is Ti:sapphire crystal.

18. A photoacoustic measurement apparatus comprising:
the multi-wavelength laser device according to claim 1; and
a photoacoustic wave detection unit that detects a photoacoustic wave generated in a subject when the subject is irradiated with the first laser light emitted from the multi-wavelength laser device and detects a photoacoustic wave generated in the subject when the subject is irradiated with the second laser light emitted from the multi-wavelength laser device.

* * * * *